United States Patent [19]
Mann

[11] Patent Number: 6,026,680
[45] Date of Patent: Feb. 22, 2000

[54] PAINT AND ADHESIVE TEST SYSTEM

[76] Inventor: George E. Mann, 1816 Oak St., South Pasadena, Calif. 91030

[21] Appl. No.: 09/343,981

[22] Filed: Jun. 30, 1999

[51] Int. Cl.$^7$ .................................................. G01B 21/08
[52] U.S. Cl. .......................................... 73/150 R; 73/827
[58] Field of Search ............................. 73/150 R, 150 A, 73/827, 54.22; 156/64

[56] References Cited

PUBLICATIONS

Specification Sheet for Model TCM1000 and Digital Model TCD1000 Test Stands, John Chatillon & Sons, Inc., 1997.
"Autotest™ Software," John Chatillon & Sons, Inc., Spec Sheet 3260/ Jan. '97.
ASTM Standard D 4541—93; Standard Test Method for Pull–off Strength of Coatings Using Portable Adhesion Testors.
Contents; 1992 Annual Book of ASTM Standards vol. 15.06 Adhesives pp. X thru XII.
"Measurement of Adhesion by a Blister Method", Journal of Applied Polymer Science, vol. V, Issue No. 14, pp. 125–134 (1961).
ASTM Standard D 1002—72 (Reapproved 1983) Standard Test Method for Strength Properties of Adhesives in Shear by Tension Loading (Metal–to–Metal), pp. 47 thru 49.
ASTM Standard D 1781—76 (Reapproved 1986) Standard Method for Climbing Drum Peel Test for Adhesives, pp. 106 thru 109.
ASTM Standard D 3806—79 (Reapproved 1984) Standard Test for Strength Properties of Adhesives in Cleavage Peel by Tension Loading (Engineering Plastics–to–Engineering Plastics), pp. 277 thru 279.

*Primary Examiner*—Hezron Williams
*Assistant Examiner*—Michael Cygan
*Attorney, Agent, or Firm*—Charles H. Thomas

[57] ABSTRACT

A testing system provides a quantitative way of measuring the adhesive strength of adhesives, paints, coatings, adhesive tapes, and other test substances to underlying adherends and substrates, such as metals. The test system of the invention consistently produces uniform results. First and second adherends are bonded together over a relatively small area near the centers and are then pulled apart by a force applied at one end of one of the adherends. The force is increased until the second adherend member is debonded from the first throughout the test bonding zone, thus determining the total energy expended in debonding the first and second adherend members plus strain energy expended in displacing the second member from the first. The force is then decreased until there is no longer any displacement of the second member from the first while concurrently measuring the decreasing force and displacement of the second adherend member from the first adherend member as a function of the decreasing force. This determines the strain energy apart from the total energy. The strain energy is then subtracted from the total energy and the resulting difference is divided by the area of the test bonding zone to determine the specific work of debonding. The strength of the adhesive properties of the test substances, and also the cohesive bonding strength of such substances may be determined utilizing the system of the invention.

21 Claims, 8 Drawing Sheets

PAINT AND ADHESIVE TEST SYSTEM

BACKGROUND OF THE INVENTION

1. Field of the Invention

The present invention relates to a testing apparatus and a method for determining the specific work of debonding and/or cohesive failure of paints and adhesives.

2. Description of the Prior Art

For many years those skilled in the art have attempted to find a suitable method for measuring the adhesive (or debonding) strength of paint which would provide results independent of the testing process. One such process is a so-called "blister" method. In this process a fluid, either gas or liquid, is injected under a coating of paint through a hole in a substrate forcing the coating to lift from the substrate in the form of a blister. One example of testing using a "blister" method is described in an article entitled, "Measurement of Adhesion by a Blister Method", published in the Journal of Applied Polymer Science, Vol. A, Issue No. 14, pp. 125–134, 1961. However, none of the known blister testing methods has been widely accepted to evaluate the debonding strength of coatings.

Various other tests have also been devised to test the adhesive properties of both paints and adhesives. The American Society of Testing Materials through its Committees D-1 and D-14 has incorporated into its ASTM Standards some of these various test procedures to evaluate the strength of paints and adhesives. However, none of these tests as yet can determine the important adhesive strength property of paints and adhesives, which is the specific work of debonding. This is a parameter that is independent of the testing process. It is a function of only the paint-substrate and adhesive-adherend combinations tested, and the surface treatment of the bond areas.

I previously developed certain testing techniques for determining the specific work of debonding. These techniques are described in my prior U.S. Pat. Nos. 5,575,868 and 5,768,936. From repeated tests, I have since discovered that the debonding zones of those systems were often noncircular, and hence the calculations of the specific work of debonding using those systems is sometimes inaccurate. However, I have now invented and tested a new system which produces uniform debonding in both paints and adhesives. This new system results in being able to calculate accurate values of the adhesive strength or internal cohesive strength of both adhesives and paints. The failure of the test substance may occur as either a failure of the adhesive bond between the test substance and the substrate employed, or as an internal cohesive failure within the substance being tested itself. In either event, the adhesive or cohesive strength is expressed as the specific work of debonding or cohesive failure.

SUMMARY OF THE INVENTION

The present invention provides a relatively simple testing method and system for paints and adhesives. It provides accurate values of the strength of paints and adhesives, and it can be used for testing under extreme conditions in an environmental chamber. The present invention corrects the problems of nonuniform debonding that occurred in the systems described in my prior U.S. Pat. Nos. 5,673,586 and 5,768,936.

The present invention, when used to evaluate the strength of an adhesive, consists of two rectangular adherends bonded by the adhesive over a relatively small area. One of the adherends has greater rigidity than the other, either due to its thickness and/or the characteristics of the material from which it is formed. The specimen is mounted in a testing machine equipped for recording and/or plotting the applied force versus its displacement. The process involves lifting one end of the relatively flexible but elastic upper adherend to separate it from the rigid lower adherend and then unloading the specimen, recording both the loading and unloading forces and the corresponding displacements. From the data, the specific work of debonding or cohesive failure of the adhesive is calculated.

The specimen is examined following testing to determine whether or not the failure has occurred at the interface between the adhesive and the adherends. If the separation is at the interface, it is the strength of the adhesive bond which has been determined. Internal cohesive failure occurs when the adhesive separates laterally laterally within itself. Occasionally, combinations of both types of failure are found in a test specimen. The English units for the specific work of debonding or cohesive failure are in-lb/sq.in.

According to the system for testing the debonding strength of an adhesive, a first elongated, rigid adherent member is covered with first and second release films, which may be lengths of adhesive tape, that are longitudinally separated from each other by a specified distance. The area of separation between the release films forms the test bonding zone surface. A layer of adhesive is applied atop the test bonding zone surface and atop those portions of the lengths of adhesive tape immediately adjacent thereto. A second adherend member is placed atop the adhesive such that a manipulative end of the second adherend member extends beyond the adhesive and so that the opposite anchored end of the second adherend member overlies a portion of the first length of adhesive tape. After bonding the two adherend members are clamped together at the anchored end of the second adherend member.

The specimen is placed in a testing machine and a force is applied to move the manipulative end of the second adherend member away from the first adherend member once the first adherend member has been firmly anchored to the base of the testing machine. The force is increased to pull the second adherend member away from the base support while concurrently measuring the increasing force and also the displacement of the second adherend member from the first as a function of the increasing force.

The same procedure is utilized to test the debonding strength of paint with the exception that the first adherend member is covered with a layer of paint and cured prior to placement of the lengths of adhesive tape. The specimen consists of a relatively flexible upper adherend and a more rigid lower substrate, which is coated with the paint being tested. To ensure that the substrate remains rigid during testing, it is sometimes necessary to provide the system with a substrate reinforcement. After the paint is cured or dried, the lengths of adhesive tape are placed atop it in spaced separation from each other. Once the lengths of adhesive tape have been placed to define the ends of the debonding zone, the layer of paint is cut transversely at the ends of the debonding zone. The lengths of adhesive tape serve as release films. An adhesive having stronger adhesive properties than the paint is then applied atop the lengths of adhesive tape and atop the paint at the test bonding zone surface between the lengths of adhesive tape. The whole assembly is then cured. A force is then applied to pull the second adherend member away from the first.

In the testing of paints, the present invention allows either the cohesive failure of the paint itself or the adhesive failure of the bond of the paint to the substrate to be determined. The adhesive or cohesive strength of the paint is evaluated with the same procedure as that used for evaluating the strength of adhesives.

The invention may be described with greater clarity and particularity by reference to the accompanying drawings.

DESCRIPTION OF THE EMBODIMENT AND IMPLEMENTATIONS OF THE METHOD

Figure 1:
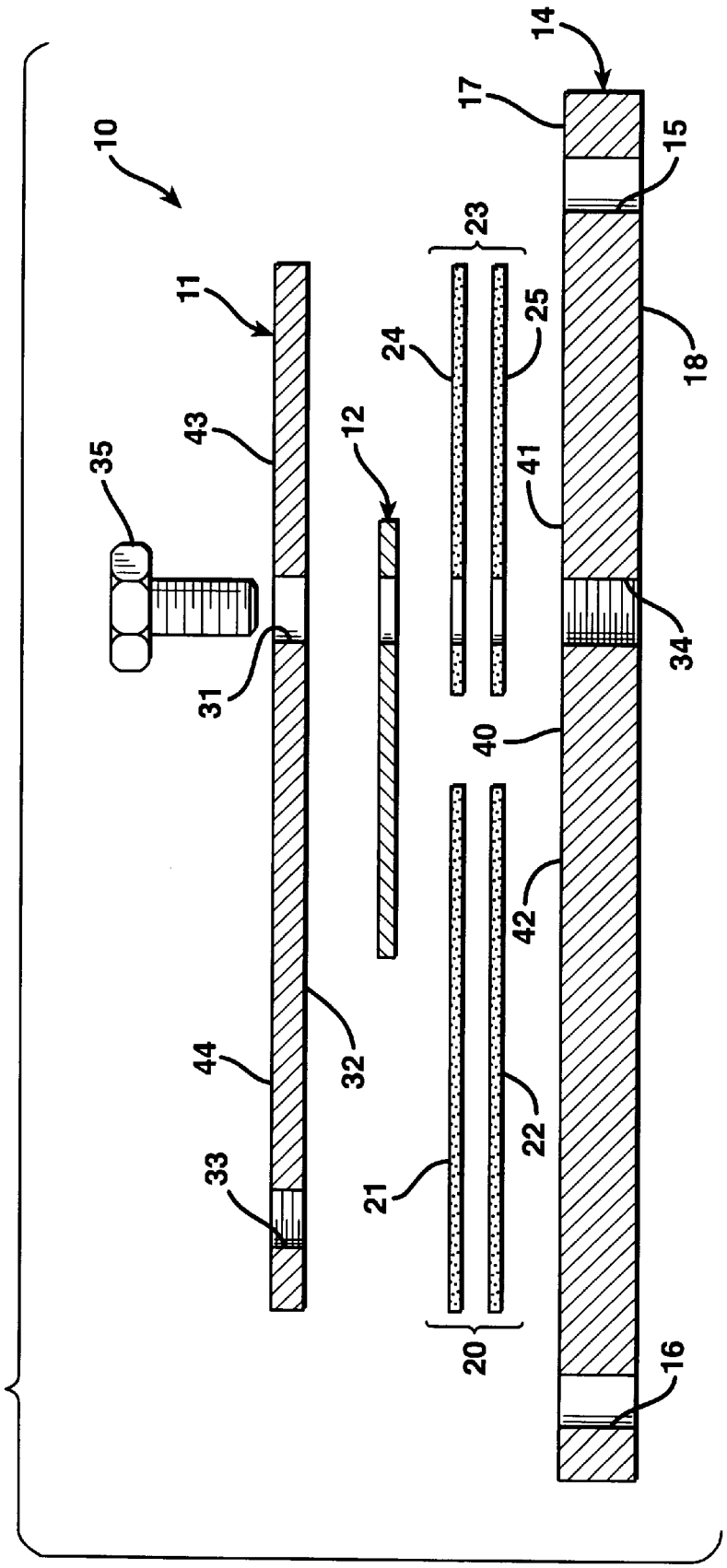
FIG. 1 is an exploded view illustrating the component layers of substances and materials employed in one embodiment of a test specimen for testing the bonding strength of an adhesive according to the invention.
Figure 2:
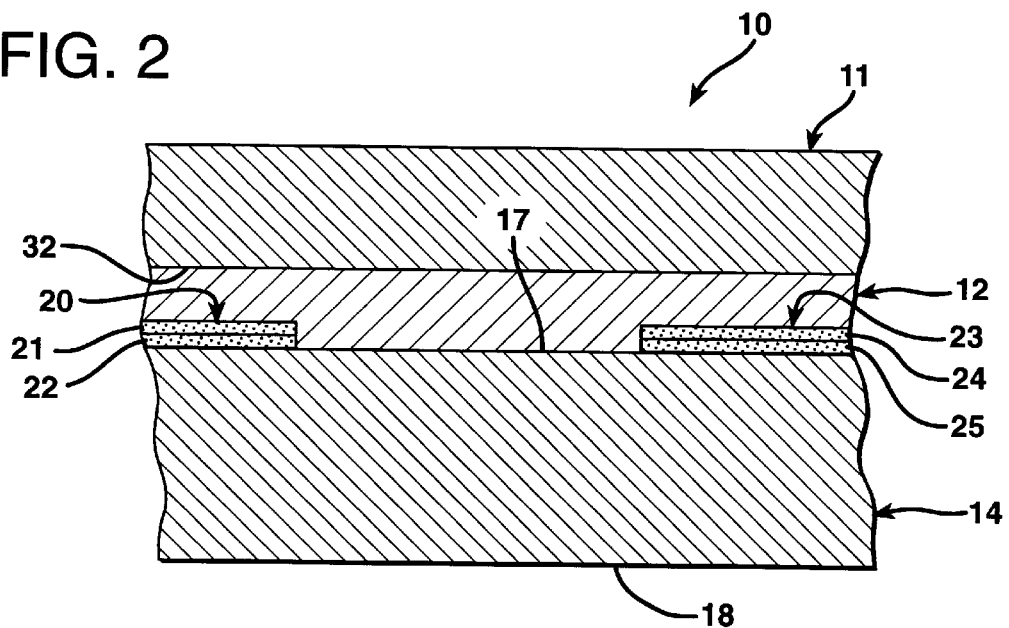
FIG. 2 is a sectional elevational detail showing the layers of component elements of FIG. 1 prior to testing as employed in the testing system according to the invention.

FIGS. 1–5 illustrate a system for testing the strength of a bond between a test substance, specifically an adhesive 12, a first, elongated, rigid adherend member 14, and a second, shorter adherend member 11. The choice of the material for the adherends is determined by the adherend of interest to which the test material 12 is likely to be applied on a commercial basis. The relatively flexible upper adherend 11 may, for example, be formed of a bar of 7075-T6 aluminum, six inches long, one inch wide and one-quarter of an inch thick. The relatively rigid lower adherend 14 may, for example, be formed of 6061-T651 aluminum. It has the same one inch width, but is eight inches long and one-half of an inch thick.

The thickness of the second or upper adherend must be great enough so that it will withstand a force large enough to debond the test material 12 and is selected to keep its stresses within the elastic or proportional limit of the material. Also, the second adherend must be thin enough so that it is sufficiently flexible to provide ample displacement for accurate recorded measurements of its deflection. If the only available material selected for the adherends is too thin or weak, the adherends should be reenforced with appropriately designed members to give sufficient flexibility to the upper unit and rigidity to the lower one.

The components of a test specimen 10 for testing the adhesive strength of the adhesive 12 are illustrated separated from each other in FIG. 1. Before the bonding of the components of the test specimen or fixture 10, laterally centered holes 15 and 16 of 0.375 inch diameter are drilled in the first adherend 14 one-half an inch from each end. Another hole 34 is drilled in the adherend 14 five inches from its left end and is internally tapped to receive a bolt 35 three-eighths of an inch in diameter and having sixteen threads per inch.

The adherend 11 has an anchored end 43 that appears on the right-hand side of the test specimen 10 in FIG. 1, and an opposite, manipulative end 44. A hole 33 is drilled and tapped in adherend 11 one-half an inch from the extremity of the manipulative left end 44 for the attachment of the coupling 71 employed in the loading text fixture 50 illustrated in FIG. 5.

Prior to testing, adherends 11 and 14 are first prepared for bonding according to the recommendations of the manufacturer of the adhesive being tested. Once the adherend 14 has been fabricated and prepared for testing, it is partially covered with a length of adhesive tape 20 three inches in length and a length of adhesive tape 23 two and one-half inches in length. These heat resistant and weak adhesive tapes may be 3M Protective Tape No. 1614, or equivalent. The length of tape 20 is comprised of a thin upper backing 21 and a layer of adhesive 22 facing the rigid adherend member 14. Similarly, the length of tape 23 is formed of a thin backing 24 with an adhesive layer 25 on its underside, also facing the adherend member 14. The length of tape 23 serves as a first release film while the length of tape 20 serves as a second release film.

The lengths of tape 20 and 23 are positioned one inch from the ends of adherend 14 and one-half an inch apart, atop adherend 14 with the release film adhesive layers 22 and 25 pressed into contact with the upper test face 17 of the adherend 14. The one-half-inch zone between the tapes 20 and 23 forms the bonding area which is the test bonding zone surface 40 of the test specimen 10. The test bonding zone surface 40 of the test specimen 10 has predetermined dimensions determined by the one inch width of the adherends 11 and 14 and a length of one-half of an inch, which is the distance between the lengths of adhesive tape 20 and 23. The testing bonding zone surface 40 is bounded longitudinally on one side on the upper test face 17 by a first adjacent surface area 41 and on the other side by a second adjacent surface area 42. The length of adhesive tape 23 covers the first adjacent surface area 41, while the length of adhesive tape 20 covers the second adjacent surface area 42.

A layer of the test substance, the adhesive 12, is applied atop the test bonding zone surface 40 and atop those portions of the first and second lengths of adhesive tape 20 and 23 immediately adjacent to the test bonding zone surface 40. Preferably, the adhesive 12 is applied on top of tapes 20 and 23 and adherend 14, so as to extend one inch beyond each side of the test bonding zone surface 40. The upper adherend 11 is then promptly positioned so that its ends are located one inch from each end of adherend 14 and so that it resides atop the entire length of the layer of adhesive 12. The whole assembly of adherends 11 and 14, lengths of tape 20 and 23, and adhesive 12 is then cured according to the specifications of the adhesive manufacturer.

Figure 3:
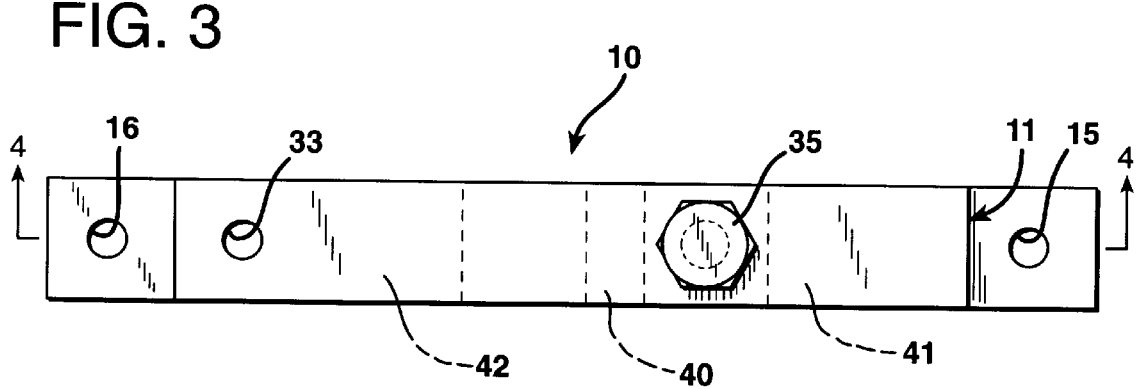
FIG. 3 is a top plan view of the component elements of FIG. 2 employed in the test system of the invention.
Figure 4:
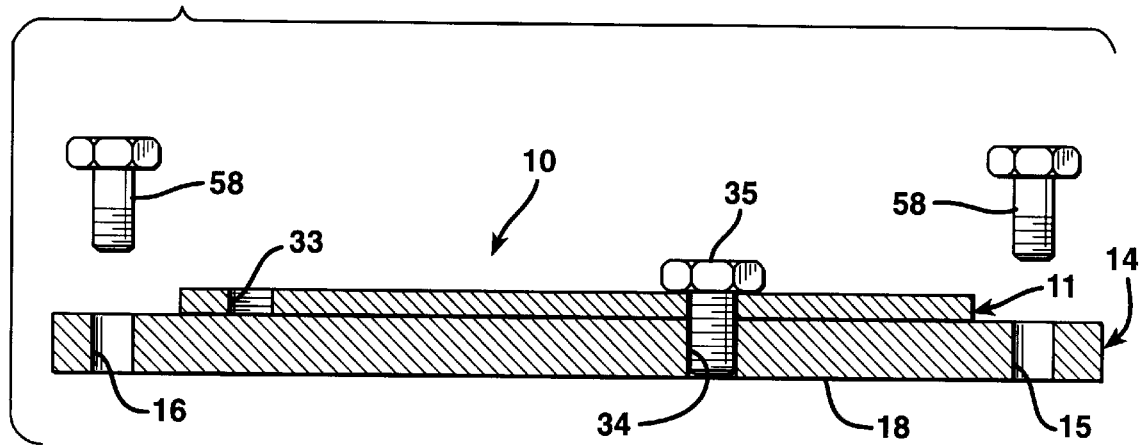
FIG. 4 is sectional elevational view taken along the line 4—4 of FIG. 3.

After the adhesive 12 has cured, the test fixture 10 is further prepared for testing as illustrated in FIGS. 3 and 4, by drilling hole 31 of 0.375 inch diameter through adherend 11, and holes through adhesive 12 and the first length of tape 23 in line with hole 34 in adherend 14. Bolt 35 is then installed to immobilize the anchored end 43 of the second adherend member 14 relative to the first adherend member 11.

Figure 5:
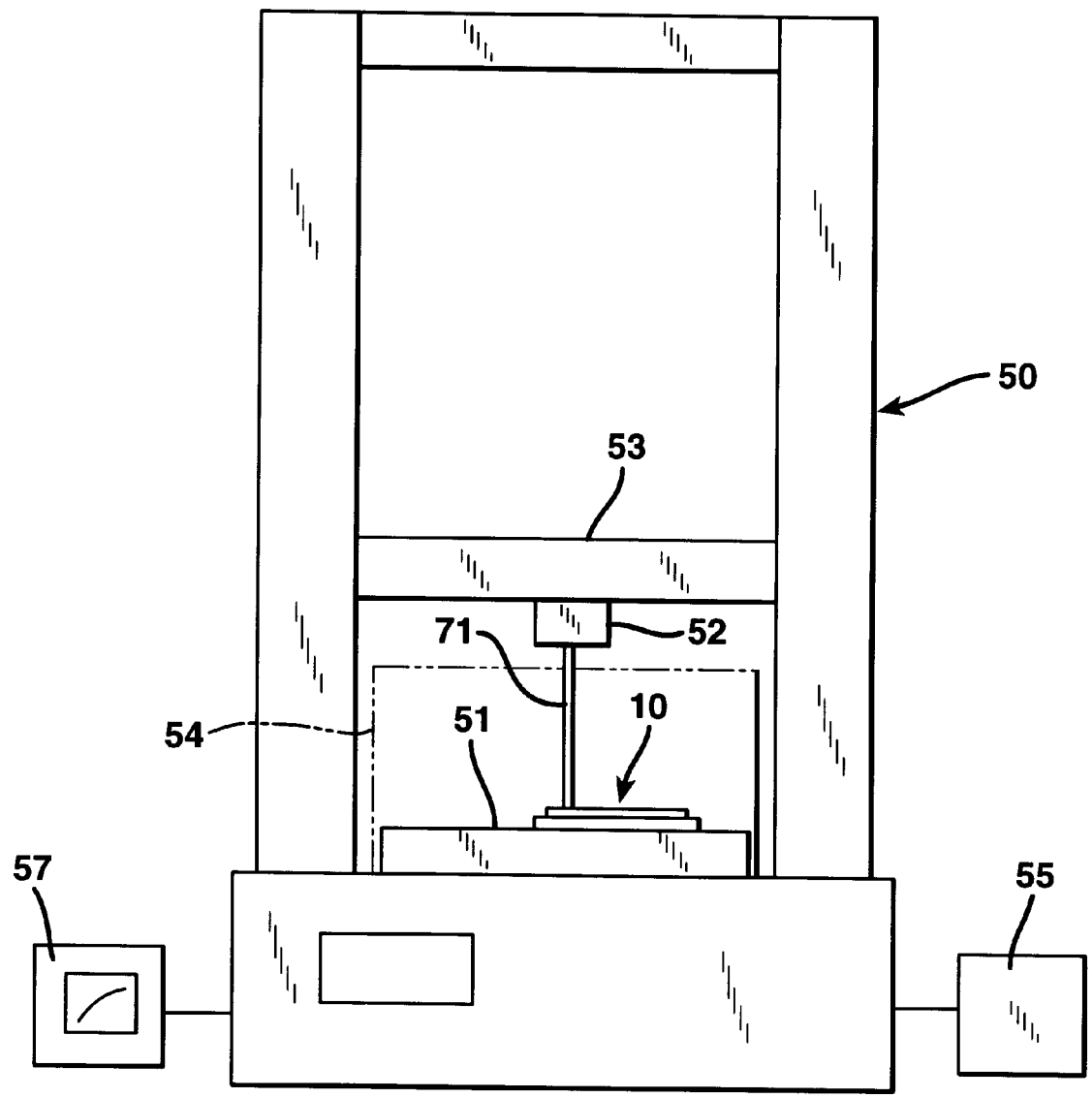
FIG. 5 is a diagrammatic view of a testing system according to the invention which includes a testing machine.

FIG. 5 illustrates diagrammatically a typical testing machine 50 loaded with the test fixture 10. The testing machine 50 may, for example, be a conventional commercially available motorized test stand for exerting forces on test materials, such as either the Model TCM 1000-SS or the digital model TCD 1000-SS Test Stand, both of which are manufactured by John Chatillon & Sons, Inc., located at 7609 Business Park Drive, Queensboro, N.C. 27409. The testing machine 50 includes a base plate 51, which serves as a base support, a ram member 53 that is movable toward or away from the base 51, a controller 55 for controlling the distance of movement of the ram member 53 from the base 51, and an instrument 57 for registering the force applied to the ram 53 throughout its movement relative to the base 51. Loading jaws 52 are attached to the underside of the ram 53 that faces the base 51. A loading rod 71 has external threads on its lower, distal end.

To test the specimen 10, the threaded end of the loading rod 71 is threadably engaged in the tapped bore 33 in the manipulative end 44 of the second adherend member 11. The proximal, upper end of the loading rod 71 is gripped in the testing machine jaws 52. The first adherend member 11 is firmly anchored to the base 51 by means of bolts 58 which extend through the holes 15 and 16 at the ends of the first adherend member 14 and into aligned tapped openings in the base 51. The test fixture 10 may be placed in a chamber 54 during testing to determine the effects of environmental conditions upon the adhesive strength of a material.

The instrument 57 of the testing machine 50 must be equipped with suitable recording equipment to compile a record of the applied load and displacement of loading rod 71 during the full cycle of loading and unloading. The instrument 57 may be a recorder, as illustrated in FIG. 5, that graphically records the displacement of the second adherend member 11 from the first adherend member 14. Alternatively, the function may be performed by a conventional personal computer programmed to record the force applied by the ram 53 to the manipulative end 44 of the second adherend member 11 while concurrently recording displacement of the manipulative end 44 of the second adherend member 11 from the first adherend member 14 as a function of the force applied by the ram 53. In a digitized system such as this, the work performed by movement of the ram 53 relative to the base 51 may be provided as an output in either graphical form, digital form, or both. The controller 55 may be a simple bidirectional power switch, or a personal computer having a keyboard input.

Regardless of whether the application and measurement of the force of the ram 53 and the displacement produced by that force in the second adherend member 11 is performed manually, by analog means, or digitally, the method for calculating the specific work of debonding is the same. Specifically, the work of debonding is the net work of debonding a substance, a coating, or an adhesive from a substrate or an adherend in a tensile fracturing process. The work of debonding must not include any strain energy of the mechanical parts of the test specimen or apparatus.

Figure 12:
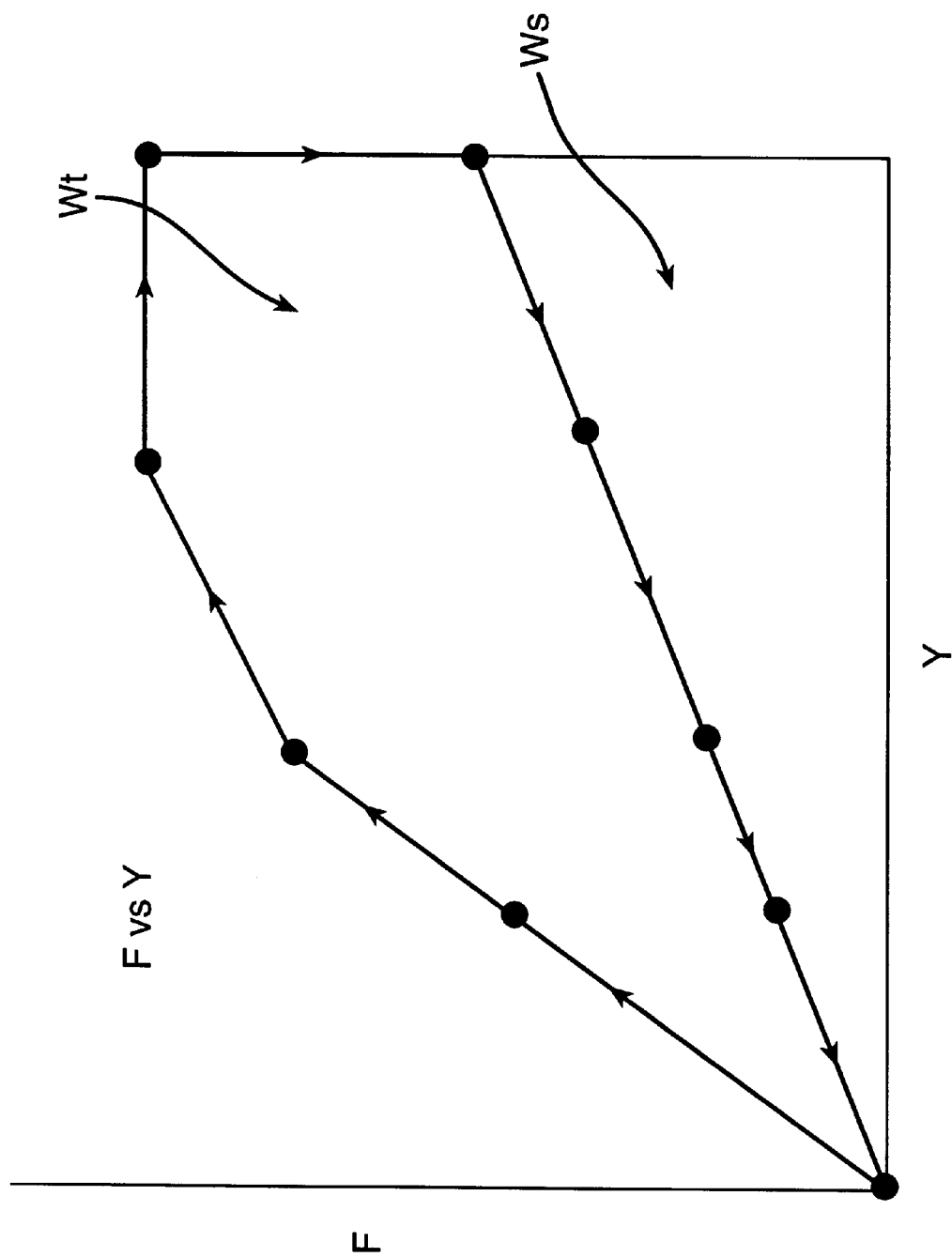
FIG. 12 is a graphical diagram illustrating the determination of specific work of debonding according to the invention utilizing the test fixture of FIG. 5.

FIG. 12 illustrates graphically the force F which is the load applied to the ram 53, versus the displacement Y, which is the movement of the manipulative end 44 of the second adherend 11 as measured in alignment with the tapped bore 33 therein.

The first step in the testing process is to slowly apply a tensile load to rod 71, recording both force and displacement, as shown in FIG. 12. The movement of the ram 53 away from the base 51 must be at a slow speed of no more than 0.020 inches per minute. The ram 53 travels away from the base 15 until the adherends 11 and 14 have separated completely at the test bonding zone surface 40 and are held together only by the bolt 35. The test specimen 10 is then slowly unloaded to zero at a speed of no more than 0.050 inches per minute, recording again the force and displacement.

The net work of debonding $W_n$ is found by subtracting the strain work $W_s$ during the step of unloading from the total work $W_t$ performed during the debonding process. $W_s$ and $W_t$ are both illustrated in FIG. 12. The specific work of debonding G is calculated by dividing the $W_n$ by the area of debonding $A_n$. In the test specimen 10 the area of debonding $A_n$ is the area of the test bonding zone surface 40, which is one-half of an inch in length by one inch in width.

The simplified graph of FIG. 12 represents the output of the test machine 50, which is available numerically and/or in the form of a plot of recorded data from the force gauge 57. The specific work of debonding is calculated by the formula $G=(W_t-W_s) \div A_n$.

The area under the recorded load vs displacement plot of FIG. 12, or the calculated area from the data, represents the total energy $W_t$ expended in debonding the adhesive 12 from the test bonding zone surface 40. Some of that energy is the strain energy $W_s$, which remains in the upper adherend and apparatus until the specimen 10 is unloaded. This energy $W_s$ is evaluated using the area under the recorded unloading plot. The net work of debonding is the difference of the two energies ($W_t-W_s$), and the specific work of debonding is found by dividing this net work by the area of the bonded zone. The specific work of debonding is in in.–lb./sq. in., if measured in English units.

After testing, the bolt 35 is removed and the adherends 11 and 14 are examined to determine the nature of the adhesive failure. If the whole separation is at the interface between the layer of adhesive 12 and either the adherend 11 or the adherend 14, the failure is a debonding failure and the strength of the adhesive bond is expressed as the specific work of debonding. On the other hand, internal cohesive failure occurs when the adhesive separates laterally within itself. It is expressed as the specific work of cohesive failure, using the same calculation procedure for adhesive strength. If there is only cohesive failure, the adhesive bonding strength is at least equal to or greater than the cohesive strength. If there is partial failure of each type over the failure zone, the two strengths are approximately equal, and evaluated using the net work of debonding and the debonded area.

Figure 6:
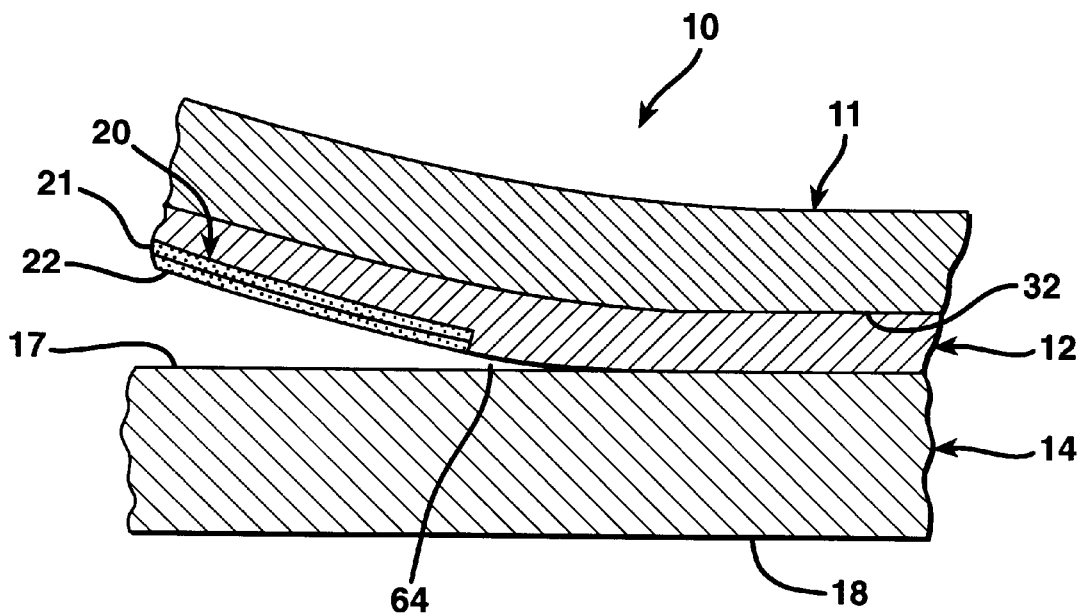
FIG. 6 is a sectional elevational detail illustrating the adhesive failure of an adhesive bond in the test components of FIG. 2 in determining the adhesive strength of a test substance according to the invention.

FIG. 6 illustrates the preliminary failure of the adhesive bond which may occur at the interface between the test adhesive 12 and the adherend 14. Prior to this event, the weak adhesive tape 20 had already debonded throughout its length with negligible resistance. Once separation has started in zone 64, it progresses slowly as the load on adherend 11 is continuously increased until the adhesive 12 has debonded throughout the area of the test bonding zone surface 40 between the tapes 20 and 23 on test face 17.

Figure 7:
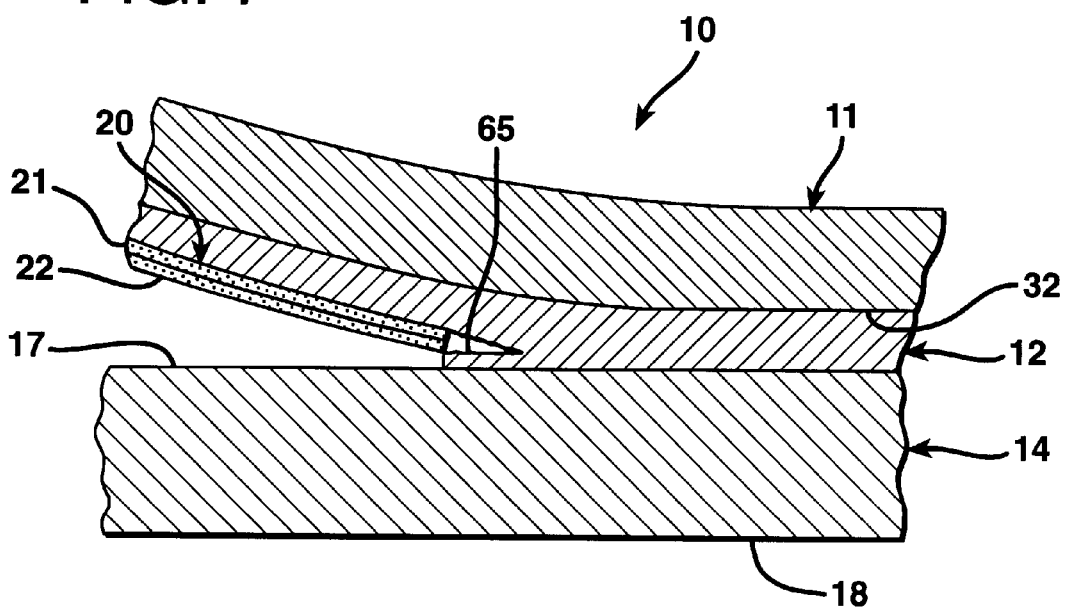
FIG. 7 is a sectional elevational detail illustrating cohesive failure in the test substance of FIG. 2 in determining the internal cohesive strength of a test substance according to the invention.

FIG. 7 illustrates the system of the invention at the first moment of cohesive failure within the test adhesive 12. As in the failure of the adhesive bond of the test adhesive 12, the weak adhesive tape 20 had already debonded before the internal separation of the test adhesive 12, indicated at zone 65. That is, a portion of the adhesive 12 remains adhesively secured to the test face 17 of the adherend 14 at the testing bonding zone surface 40, but the portion immediately adjacent thereto gives way and a fracture forms within the structure of the test adhesive 12. It is observed that occasionally there is a combination of adhesive and cohesive failures; that is, when there is evidence of both types of failure within the debonding zone.

Figure 8:
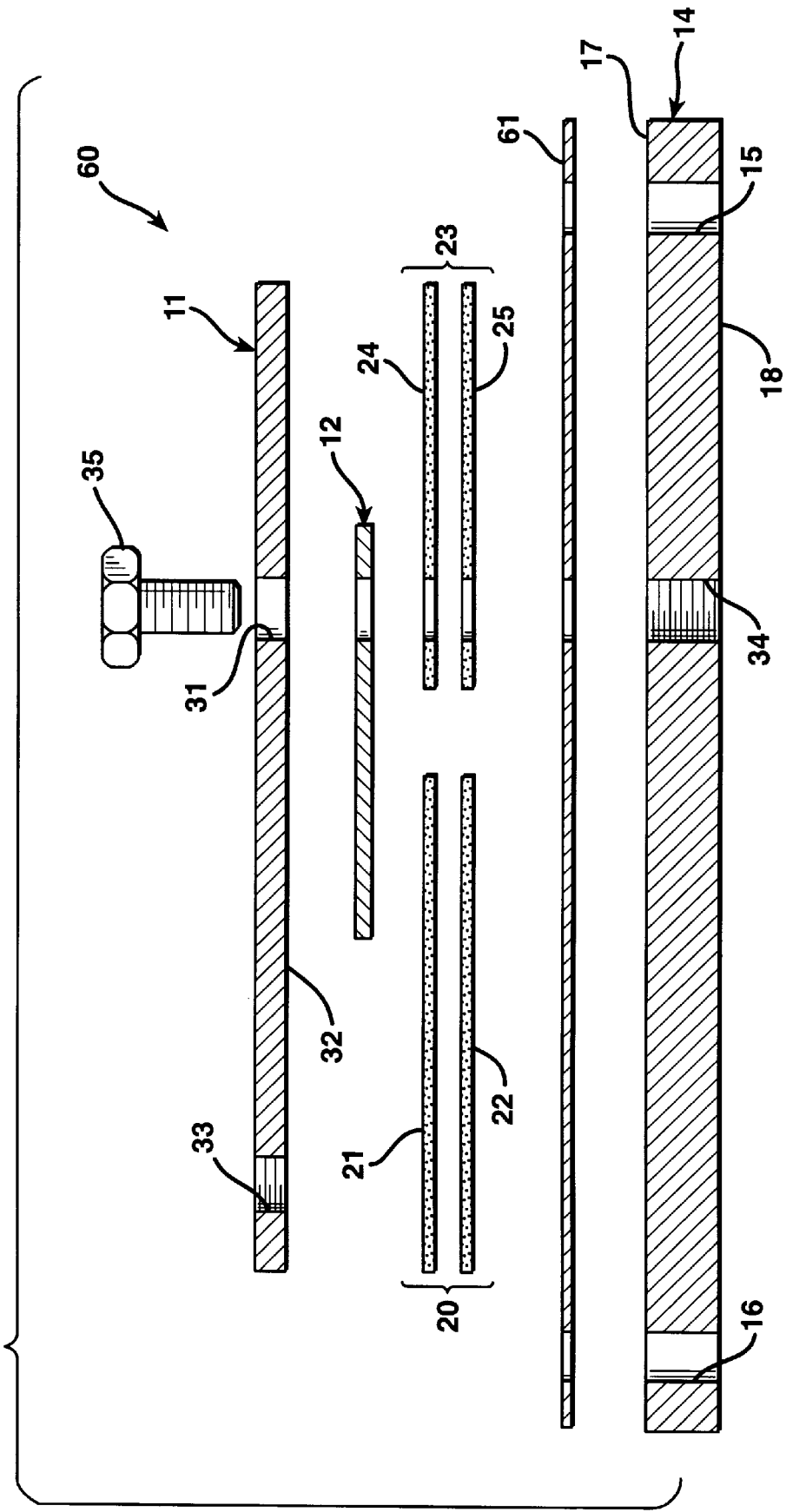
FIG. 8 is an exploded elevational view illustrating the layers and component elements of a test specimen for testing the bonding strength of a coating of paint according to the invention.
Figure 9:
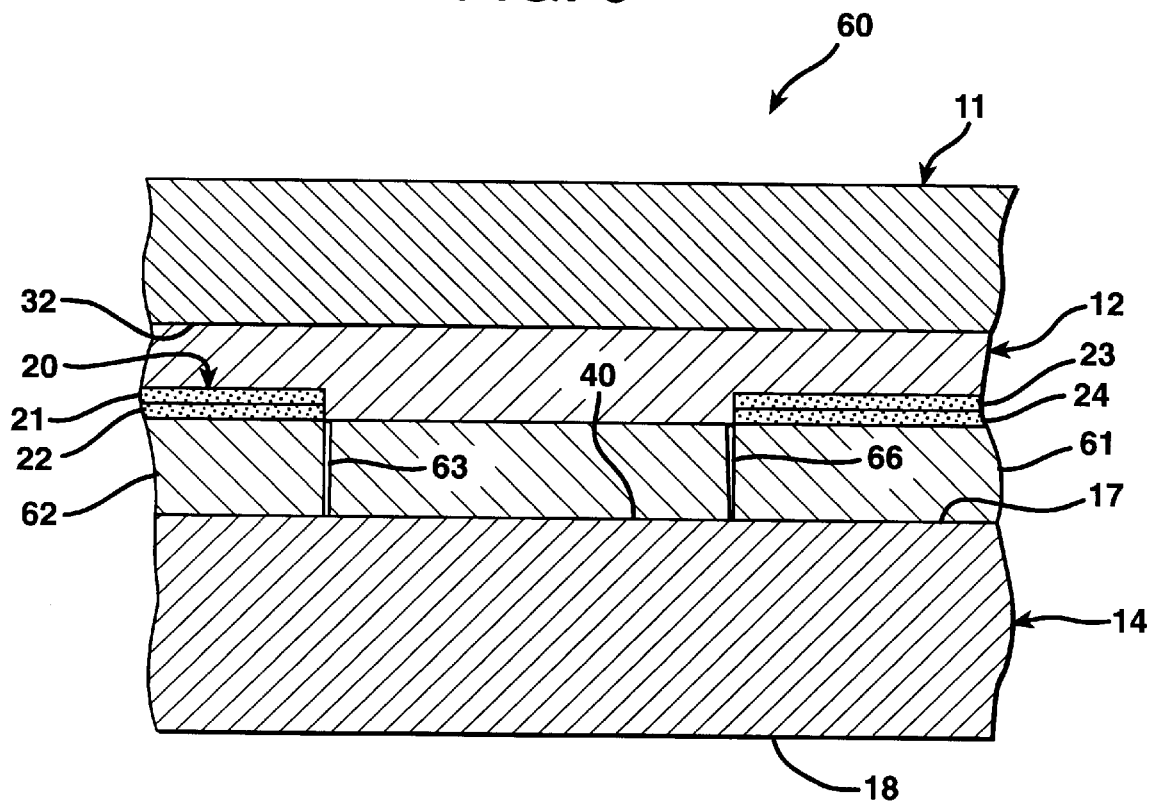
FIG. 9 is a sectional elevational detail illustrating the layers of component elements of FIG. 8 prior to testing.

FIGS. 8 and 9 illustrate a system of the invention for testing the strength of the bond between a test coating of paint 61 and the substrate 14. Test specimen 60 has many of the same elements and details as test fixture 10 in FIG. 1, and components common to both of these test specimens bear the same reference numbers. All the holes in test fixture 60 have the same sizes and locations as specified for test fixture 10. The tapes 20 and 23 are the same type and size as used for test fixture 10. The choice of the material for the substrate or adherend 14 is determined by the substrate of interest to which the test coating 61 is likely to be applied on a commercial basis. The thickness of the substrate 14 must be ample to maintain rigidity during the test, and may be reenforced with a doubler if necessary. The substrate 14 may, for example, be formed of a bar of 6061-T651 aluminum, one inch wide and one-half inch thick.

The adherend 11 and adhesive 12 must be selected to provide a stronger bond than that expected or found in the bond of the paint coating 61 to substrate 14. As in the case of testing adhesives, the adherend 11 must be selected to keep its stresses within the elastic proportional limit of the material, but still be sufficiently flexible to provide ample measurable displacement under load.

The adherend 11 and substrate 14 are machined exactly as was done for the adhesive test adherends 11 and 14 in the test specimen 10. Adherend 11 is chemically treated for bonding with adhesive 12. Substrate 14 is treated according to the specifications of the manufacturer of the paint coating 61 prior to application of the layer of paint 61 and prior to testing. The coating 61 is applied across the entire upper test face 17 of substrate 14 and then cured according to the specifications of the paint manufacturer.

Once the paint coating 61 has cured, the tapes 20 and 23 are positioned one inch from the ends of substrate 14 and one-half an inch apart. The film adhesive layers 22 and 25 are pressed against the coating 61. The one-half-inch long zone 40 between the tapes 20 and 23 forms the bonding area of the test specimen. As shown in FIG. 9, straight, transversely extending grooves 63 and 66 are cut into the coating 61 with a sharp tool across the width of the coating 61 adjacent to the ends of the lengths of tape 20 and 23.

A layer of adhesive 12 having stronger adhesive properties than the paint coating 61 is applied on top of tapes 20 and 23 and on top of the coating 61. The layer of adhesive 12 preferably extends one inch beyond each side of the test bonding zone surface 40. The whole test specimen 60 of coated substrate 14, tapes 20 and 23, adhesive 12, and adherend 11 is then cured according to the specifications of the adhesive manufacturer.

After the adhesive 12 has cured, the bonded test fixture 60 is further prepared for testing as illustrated in FIGS. 8 and 9, by drilling hole 31 of 0.375 inch diameter through adherend 11, adhesive 12 and tape 23 in line with hole 34 in substrate 14. Bolt 35 is then installed.

The test stand arrangement for the test fixture 60 is identical to that shown in FIG. 5 for the testing of test fixture 10, and the test procedure and analysis of results is identical to those previously described. Test fixture 60 may be placed in a chamber 54 during testing to determine the effects of environmental conditions upon the bonding strength of a coating.

Figure 10:
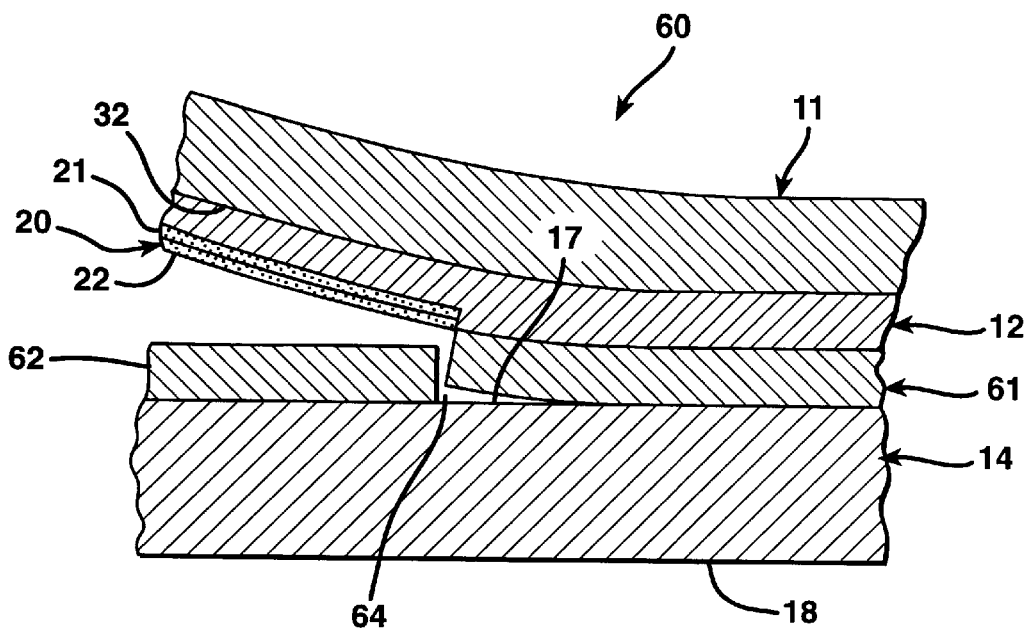
FIG. 10 is a sectional elevational detail illustrating the failure of an adhesive bond in the test components of FIG. 9 in determining the adhesive strength of a coating of paint according to the invention.

The failure of the coating 61 may occur as an adhesive failure, a cohesive failure, or a combination of each. FIG. 10 illustrates the preliminary failure of the adhesive bond between the coating 61 and the substrate 14, where the weak adhesive tape 20 had already debonded. Once separation has commenced in zone 64, it progresses slowly as the load on adherend 11 continuously increases until coating 61 has debonded from substrate 14 over the complete area 40 between the tapes 20 and 23.

Figure 11:
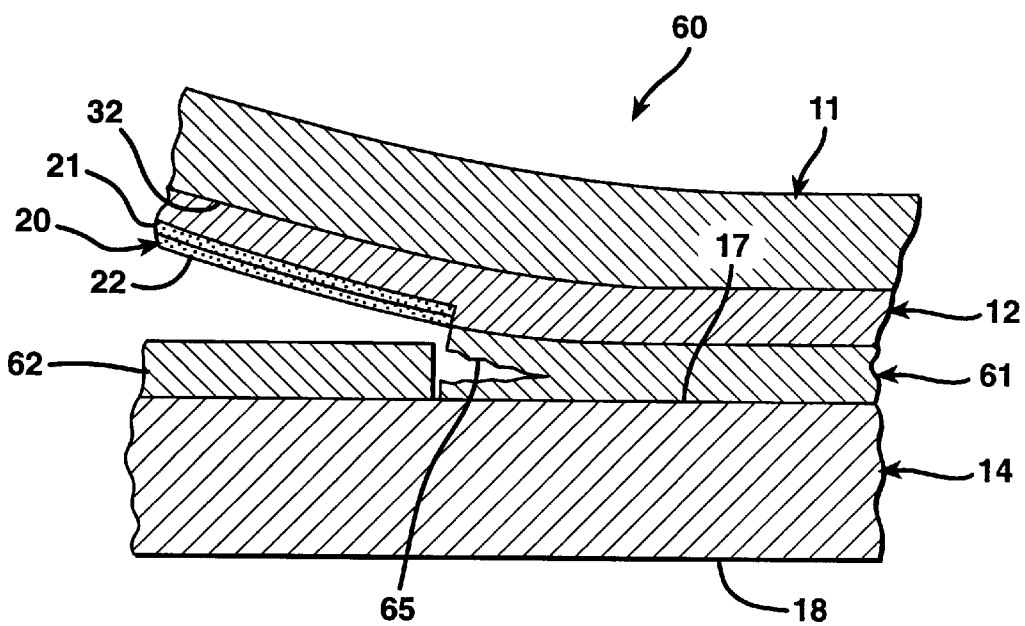
FIG. 11 is a sectional elevational detail illustrating the cohesive failure in determining the internal cohesive strength of a coating of paint shown in FIG. 9 according to the invention.

FIG. 11 illustrates the system of the invention at the moment of cohesive failure within the coating 61. As in the failure of the adhesive bond of the coating 61, the adhesive tape 20 has already debonded. This cohesive failure occurs due to internal separation within the coating 61, indicated at zone 65. That is, a portion of the paint coating 61 remains adhesively secured to the test face 17 of the substrate 14, but the portion immediately adjacent thereto gives way and a fracture forms within the structure of the paint coating 61. With coatings, as with adhesives, occasionally there is a combination of adhesive and cohesive failures. The evaluations of the specific work of debonding or cohesive failure of coatings are found using the same procedure as for adhesives.

Paint is not the only type of test substance for which the adhesive properties may be measured in the system illustrated in FIGS. 8–11. To the contrary, the test substance 61 illustrated in those drawing figures may be a coating, such as a varnish, shellac, glaze, or any other material that will adhere to the test adherend 14. Alternatively, the test substance 61 may be a test specimen of adhesive tape that adheres to the test adherend 14. The use of other materials as the test substance 61 is also within the scope of the invention.

Undoubtedly, numerous variations and modifications of the invention will become readily apparent to those familiar with adhesion testing systems. For example, any number of different materials may be used to form the adherends or substrate, the test substance itself, and the adhesive tapes that define the test bonding zone surface. Accordingly, the scope of the invention should not be construed as limited to these specific embodiments of the invention depicted nor the specific implementations of the method described.

I claim:

1. A system for testing adhesive strength comprising:
   a first elongated, rigid adherend member having a test bonding zone surface of predetermined dimensions bounded longitudinally on one side by a first adjacent surface area and on the other side by a second adjacent surface area;
   first and second release films respectively covering said first and second adjacent surface areas and leaving said test bonding zone surface therebetween uncovered by said release films;
   a layer of test substance applied atop said test bonding zone surface and atop those portions of said first and second release films immediately adjacent to said test bonding zone surface;

a second adherend member having an anchored end and a manipulative end positioned atop said layer of test substance so that said manipulative end extends therebeyond to contact at least a portion of said second release film and so that said anchored end overlies at least a portion of said first adjacent surface area of said first adherend;

an adherend clamp that immobilizes said anchored end of said second adherend member relative to said first adherend member; and a testing machine including a base to which said first adherend member is firmly anchored, a ram member movable toward and away from said base, a controller for controlling the distance of movement of said ram member from said base, and a force gauge for registering the force applied to said ram throughout its movement relative to said base, and a coupling that rigidly connects said manipulative end of said second adherend to said ram.

2. The system according to claim 1 wherein said second adherend member is constructed of a material that remains within its elastic limit throughout the application of said force.

3. The system according to claim 1 wherein said adherend clamp is comprised of a bolt that passes through said second adherend member and which is threadably engaged in the structure of said first adherend member.

4. The system according to claim 1 wherein said first adherend member has ends that extend longitudinally in opposite directions beyond said second adherend members, beyond said layer of test substance, and beyond said first and second films and further comprising fixture clamps that secure said ends of said first member to said test fixture base.

5. The system according to claim 1 wherein said first and second release films are both formed of lengths of adhesive tape, each having a layer of pressure-sensitive adhesive that contacts said first adherend member.

6. The system according to claim 1 wherein a tapped bore is defined in said manipulative end of said second member and said coupling has external threads thereon and is threadably engaged in said tapped bore in said manipulative end of said second adherend member.

7. The system according to claim 1 wherein said first adherend member is more rigid than said second adherend member.

8. A system for testing adhesive strength comprising:

a first elongated, rigid adherend member having a test bonding zone surface of predetermined dimensions bounded longitudinally on one side by a first adjacent surface area and on the other side by a second adjacent surface area;

a layer of test substance applied atop said test bonding zone surface and atop at least those portions of said first and second surface areas immediately adjacent to said test bonding zone surface;

first and second release films respectively covering those portions of said layer of test substance applied to said first and second adjacent surface areas and leaving that portion of said layer of said test substance that is applied to said test bonding zone surface therebetween uncovered by said release films;

a layer of adhesive having stronger adhesive properties than said test substance applied to said portion of said layer of said test substance that is applied to said test bonding zone surface;

a second adherend member having an anchored end and a manipulative end positioned atop said layer of test substance so that said manipulative end extends beyond said layer of adhesive and so that said anchored end overlies at least a portion of said first adjacent surface area of said first adherend, wherein said layer of adhesive is bonded to both said second adherend member and to said portion of said test substance applied to said test bonding zone surface;

an adherend clamp that immobilizes said anchored end of said second adherend member relative to said first adherend member; and a testing machine including a base to which said first adherend member is firmly anchored, a ram member movable toward and away from said base, a controller for controlling the distance of movement of said ram member from said base, a force gauge for registering the force applied to said ram throughout its movement relative to said base, and a coupling that rigidly connects said manipulative end of said second adherend to said ram.

9. The system according to claim 8 wherein said first adherend member has greater rigidity than said second adherend member and said second adherend member is constructed of a material that remains within its elastic limit throughout the application of said force.

10. The system according to claim 8 wherein said adherend clamp is comprised of a bolt that passes through said second adherend member and which is threadably engaged in the structure of said first adherend member.

11. The system according to claim 8 wherein said first adherend member has ends that extend longitudinally in opposite directions beyond said second adherend member and beyond said first and second release films and further comprising fixture clamps that secure said ends of said first member to said test fixture base.

12. The system according to claim 8 wherein said first and second release films are both formed of lengths of adhesive tape, each having a layer of pressure-sensitive adhesive that contacts said test substance.

13. The system according to claim 8 wherein a tapped bore is defined in said manipulative end of said second member and said coupling has external threads thereon and is threadably engaged in said tapped bore in said manipulative end of said second adherend member.

14. The system according to claim 8 wherein said test substance is comprised of paint.

15. The system according to claim 8 wherein said test substance is comprised of a coating.

16. The system according to claim 8 wherein said test substance is comprised of an adhesive tape.

17. A method of testing the adhesive strength of a test substance relative to an adherend material comprising:

securing a first rigid member formed of an adherend material to a fixed base support leaving an elongated test surface of said first adherend member exposed;

placing first and second release films atop different portions of said test surface of said first adherend member thereby leaving a test bonding zone of said test surface having predetermined dimensions uncovered between said first and second release films;

applying said test substance in liquid form in a layer that covers said test bonding zone completely and that covers those portions of said first and second release films lying immediately adjacent to said test bonding zone as well;

placing a second member formed of an adherend material atop said layer of said test substance so as to completely overlie said test bonding zone and said portions of said first and second release films lying immediately adjacent to said test bonding zone as well;

curing said layer of said test substance so that it bonds to said first rigid member at said test bonding zone and also to said second member throughout surfaces of mutual contact therebetween, thereby bonding said first and second members together throughout said test bonding zone;

clamping said first and second members immovably together at a location in registration with said first release film;

applying and increasing a force to pull said second member away from said base support and said first member at a location in registration with said second release film while concurrently measuring said increasing force and displacement of said second member from said first member as a function of said increasing force until said second member is debonded from said first member throughout said test bonding zone to determine the total energy expended in debonding said first and second members plus strain energy expended in displacing said second member from said first member;

decreasing said force until there is no longer any displacement of said second member from said first member while concurrently measuring said decreasing force and displacement of said second member from said first member as a function of said decreasing force to ascertain said strain energy apart from said total energy;

subtracting said strain energy from said total energy to determine only the energy expended in debonding said first and second members; and determining the specific work of failure of the bond between said first and second members by dividing said energy expended in debonding said first and second members by the area of said test bonding zone.

18. A method according to claim 17 further comprising detecting a drop in resistance to displacement of said first and second members that occurs when said second member is debonded from said first member, and thereupon decreasing said force as aforesaid in response to said drop in resistance.

19. A method according to claim 17 further comprising unclamping said first and second members and examining said first and second members for the extent of presence of said test substance thereon to determine if said test substance exhibits evidence of cohesive failure within said test substance.

20. A method of testing the strength of the bond of a test substance to an adherent material comprising:

securing a first rigid member formed of an adherend material to a fixed base support;

applying said test substance in liquid form in a layer on a test surface of said first rigid member, curing said layer of said test substance so that it bonds to said test surface thereof, placing first and second release films atop different portions of said layer of test substance thereby leaving a test bonding zone of said test substance having predetermined dimensions uncovered between said first and second release films;

cutting through said layer of said test substance at both sides of said test bonding zone immediately adjacent to both said first and second release films, applying a coating in liquid form of an adhesive having adhesive properties greater than those of said test substance in a layer atop at least that portion of said test substance bonded to said test bonding zone and atop at least those portions of said first and second release films immediately adjacent to said test bonding zone;

placing a second member atop said layer of adhesive curing said adhesive so that it bonds to both said second member and to said portion of said test substance bonded to said test bonding zone to thereby form an adhesive bond between said second rigid member and said test substance at said test bonding zone;

clamping said first and second members immovably together at a location in registration with said first release film;

applying a force to pull said second member away from said base support and said first member at a force application location on said second member which is in registration with said second release film and increasing said force while concurrently measuring said increasing force and displacement of said second member from said first member as a function of said increasing force until the bond of said test substance to said first member fails throughout said test bonding zone to determine the total energy expended in causing failure of said bond of said test substance to said first member throughout said test bonding zone plus strain energy expended in displacing said second member of said first member;

decreasing said force until there is no longer any displacement of said second member from said first member and concurrently measuring said decreasing force and displacement of said second member from said first member as a function of said decreasing force to ascertain said strain energy apart from said total energy;

subtracting said strain energy from said total energy to determine the energy expended in causing failure of said bond of said test substance to said first member throughout said test bonding zone; and determining the specific work of failure of the bond of said test substance to said first member by dividing said energy expended in causing failure of said bond of said test substance to said first member by the area of said test bonding zone.

21. A method according to claim 19 further comprising detecting a drop in resistance to displacement of said first and second members that occurs when said bond of said test substance to said first member fails throughout said test bonding zone, and thereupon decreasing said force as aforesaid in response to said drop in resistance.

* * * * *